(12) United States Patent  
Porter et al.

(10) Patent No.: US 7,473,529 B1  
(45) Date of Patent: Jan. 6, 2009

(54) SYSTEM AND METHOD FOR DETECTING CELLS OR COMPONENTS THEREOF

(75) Inventors: Marc D. Porter, Ames, IA (US); Robert J. Lipert, Ames, IA (US); Robert T. Doyle, Ames, IA (US); Desiree S. Grubisha, Corona, CA (US); Salma Rahman, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 279 days.

(21) Appl. No.: 11/095,098

(22) Filed: Mar. 31, 2005

Related U.S. Application Data

(60) Provisional application No. 60/558,227, filed on Mar. 31, 2004.

(51) Int. Cl.  
*C12Q 1/68* (2006.01)

(52) U.S. Cl. .............................. 435/6; 435/29

(58) Field of Classification Search .................. None  
See application file for complete search history.

(56) References Cited

U.S. PATENT DOCUMENTS

| | | | |
|---|---|---|---|
| 4,905,169 A | 2/1990 | Buican et al. | |
| 6,139,800 A | 10/2000 | Chandler | |
| 6,140,054 A * | 10/2000 | Wittwer et al. | 435/6 |
| 6,140,500 A * | 10/2000 | Yan et al. | 544/99 |
| 6,165,739 A | 12/2000 | Clatch | |
| 6,248,590 B1 | 6/2001 | Malachowski | |
| 6,304,584 B1 * | 10/2001 | Krupke et al. | 372/22 |
| 6,335,173 B1 * | 1/2002 | Kaplan | 435/7.2 |
| 6,473,171 B1 | 10/2002 | Buttry et al. | |

* cited by examiner

*Primary Examiner*—James S Ketter  
(74) *Attorney, Agent, or Firm*—Carol Larcher; Larcher & Chao LLP

(57) ABSTRACT

A system and method for detecting a detectably labeled cell or component thereof in a sample comprising one or more cells or components thereof, at least one cell or component thereof of which is detectably labeled with at least two detectable labels. In one embodiment, the method comprises: (i) introducing the sample into one or more flow cells of a flow cytometer, (ii) irradiating the sample with one or more light sources that are absorbed by the at least two detectable labels, the absorption of which is to be detected, and (iii) detecting simultaneously the absorption of light by the at least two detectable labels on the detectably labeled cell or component thereof with an array of photomultiplier tubes, which are operably linked to two or more filters that selectively transmit detectable emissions from the at least two detectable labels.

4 Claims, 7 Drawing Sheets

SYSTEM AND METHOD FOR DETECTING CELLS OR COMPONENTS THEREOF

CROSS-REFERENCE TO RELATED PATENT APPLICATIONS

This patent application claims the benefit of U.S. Provisional Patent Application No. 60/558,227, filed Mar. 31, 2004, the entire content of which is incorporated herein by reference.

STATEMENT REGARDING FEDERALLY SPONSORED RESEARCH AND DEVELOPMENT

This invention was supported in part by the U.S. Department of Energy, Grant No. W-7405-ENG-82, and the U.S. Department of Agriculture, Grant No. 2002-35201-12659. The Government may have certain rights in this invention.

BACKGROUND OF THE INVENTION

1. Field of the Invention

The present invention relates to a method for detecting a detectably labeled cell or component thereof in a sample comprising one or more cells or components thereof, at least one cell or component thereof of which is detectably labeled with at least two detectable labels, and a system for use in such a method. Immunoassay, fluorescence, and flow cytometry are employed.

2. Description of the Related Art

Various assays for determining qualitative and/or quantitative characteristics of cells or components thereof are known in the art. Flow cytometers, for example, are used in both diagnostics and research laboratories to classify and analyze cells and components thereof. In flow cytometry, cells or components thereof are typically stained with detectable fluorescent labels and are passed in a liquid suspension through a flow cell along with a sheath fluid, such that cells or components thereof are forced by hydrodynamic focusing to flow in single file along the center axis of the flow cell. A focused light beam, such as a laser beam, then illuminates the cells or components as they flow through the examination zone of the flow cell. Optical detectors within the flow cytometer measure certain characteristics of the light as it interacts with the cells or components thereof. Commonly used flow cytometers, such as the Becton-Dickinson Immunocytometry Systems "FACSCAN" (San Jose, Calif.), for example, can measure forward light scatter (generally correlated with the refractive index and size of the particle being illuminated), side light scatter (generally correlated with the particle's size), and fluorescence at one or more wavelengths. Flow cytometers and various techniques for their use are described, generally in "Practical Flow Cytometry" by Howard M. Shapiro (Alan R. Liss, Inc., 1985) and "Flow Cytometry and Sorting, Second Edition" edited by Melamed et al. (Wiley-Liss, 1990).

While flow cytometry techniques have advanced greatly over the years, efficient single-step assay processes for simultaneously detecting multiple types of cells or components thereof, and for simultaneously identifying multiple characteristics of individual cells or components thereof, remain highly desirable in the art. It would be desirable, for example, to have adequate methods and systems for performing reliable and sensitive real-time multiple determinations, simultaneously, through a single or limited step assay process. A capability to perform simultaneous, multiple determinations in a single assay process is known as "multiplexing" and a process to implement such a capability is a "multiplexed assay."

Conventional flow cytometers, to this point, have yielded a limited capacity to perform real-time multiple determinations. This is due mainly to an inability of conventional flow cytometers to receive, compute, and/or store simultaneous detection data. Moreover, conventional detection and enumeration techniques for cells or components thereof that utilize antibody-conjugated detectable labels typically yield unsatisfactory and unreliable cell or component counts due to antibody aggregations, which yield substantial "false positives."

Thus, in view of the above, there remains a need for sensitive and reliable methods and systems for the detection and enumeration of cells or components thereof. The present invention seeks to provide such a method and system. These and other objects and advantages of the present invention, as well as additional inventive features, will become apparent to those of ordinary skill in the art upon reading the detailed description set forth herein.

SUMMARY OF THE INVENTION

The present invention provides a method for detecting, distinguishing, and/or quantifying at least one detectably labeled cell or component thereof in a sample comprising one or more cells or components thereof, at least one cell or component thereof of which is detectably labeled with at least two detectable labels. The method comprises: (i) introducing a sample comprising one or more cells or components thereof, at least one cell or component thereof of which is detectably labeled with at least two detectable labels, into one or more flow cells of a flow cytometer, (ii) irradiating the sample with one or more light sources that are absorbed by the at least two detectable labels, the absorption of which is to be detected, and (iii) detecting simultaneously the absorption of light by the at least two detectable labels on the detectably labeled cell or component thereof with an array of photomultiplier tubes, which are operably linked to two or more filters that selectively transmit detectable emissions from the at least two detectable labels. The two or more filters and the array of photomultiplier tubes are operably linked to the one or more light sources by one or more optical bodies that project the detectable emissions from the at least two detectable labels to the two or more filters. The simultaneous detection of absorption of light by the at least two detectable labels indicates the presence of a detectably labeled cell or component thereof in the sample.

The present invention further provides a system for use in the above method. The system comprises: (i) two or more flow cells, into which can be placed a sample comprising one or more cells or components thereof, at least one cell or component thereof of which is detectably labeled with at least two detectable labels, (ii) one or more light sources that are absorbed by the at least two detectable labels, the absorption of which is to be detected, and (iii) an array of photomultiplier tubes, which are operably linked to two or more filters that selectively transmit detectable emissions from the at least two detectable labels. The two or more filters and the array of photomultiplier tubes are operably linked to the one or more light sources by one or more optical bodies, which project the detectable emissions from the at least two detectable labels to the two or more filters.

DETAILED DESCRIPTION OF THE INVENTION

Figure 1:
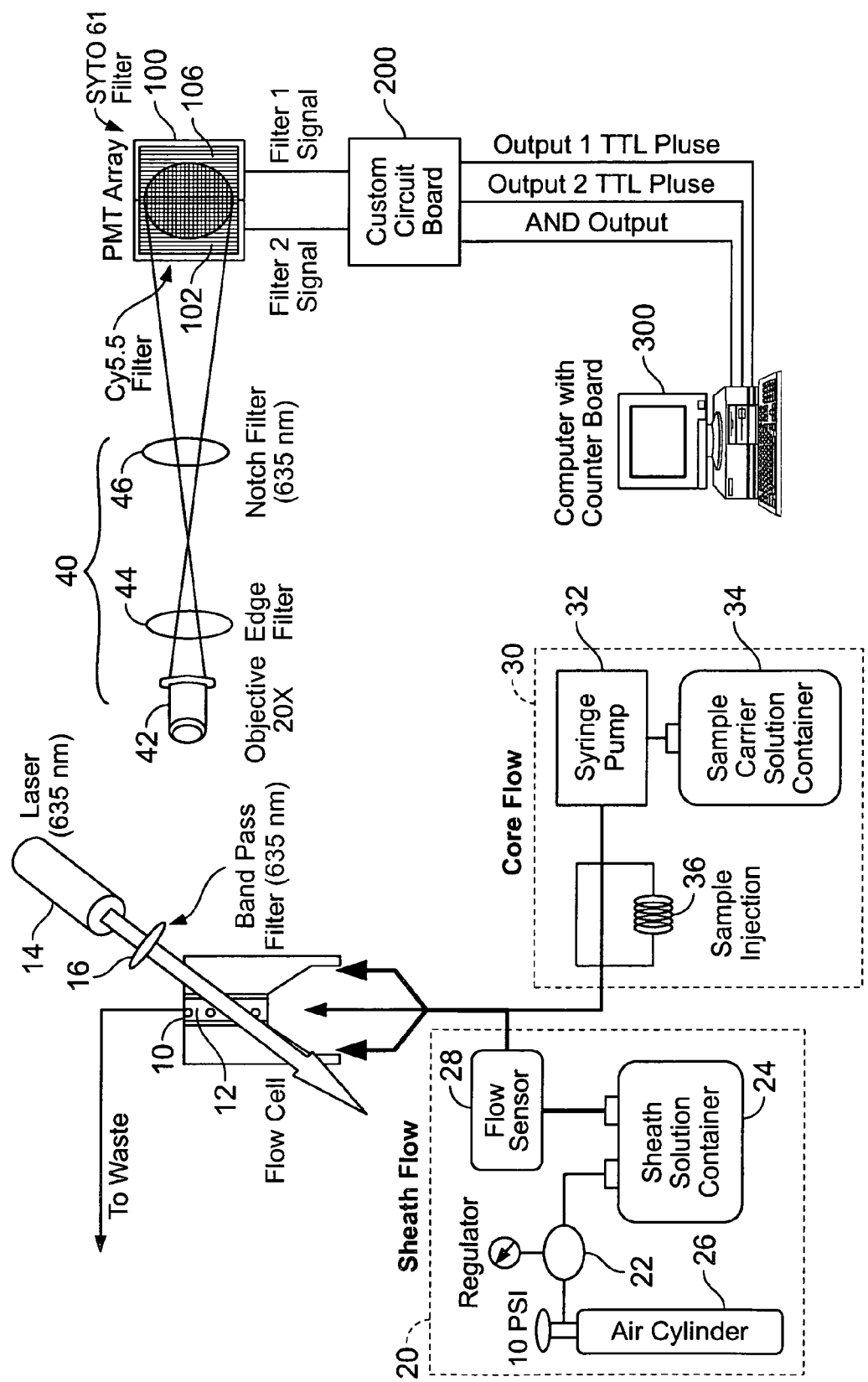
FIG. 1 is a diagram of a system for detection of cells or components thereof, according to an embodiment of the present invention.
Figure 2:
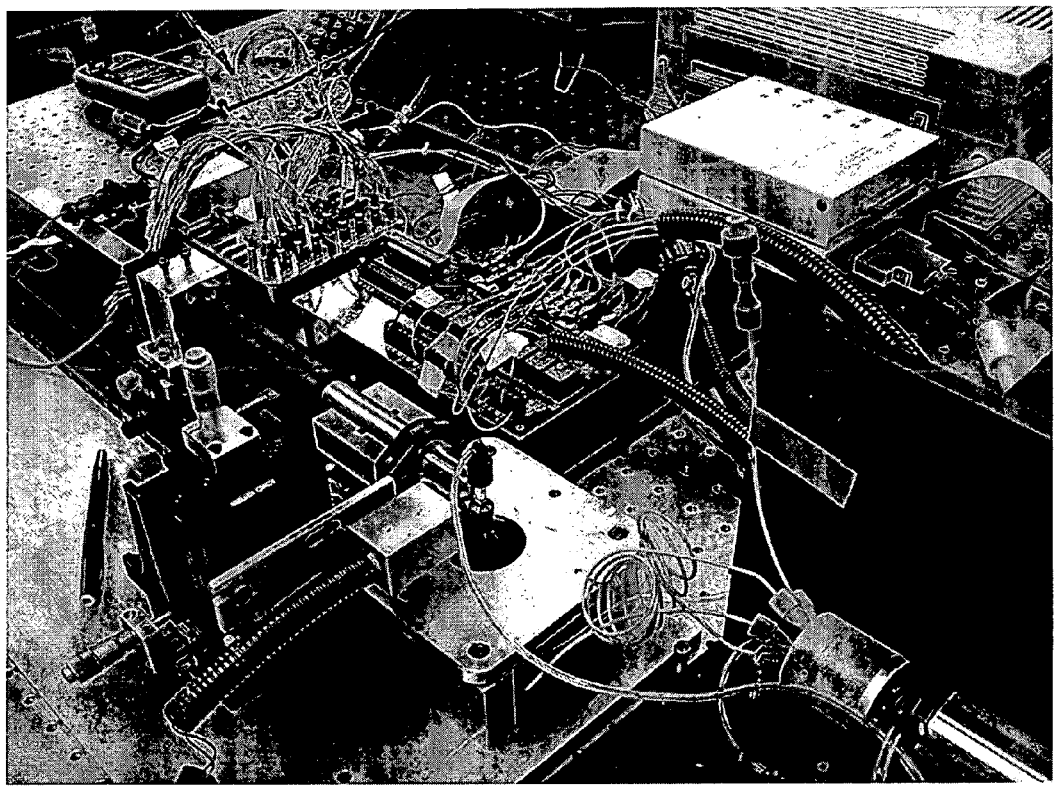
FIG. 2 is a photograph of a system for detection of cells or components thereof.

The present invention provides a method and system for detecting, distinguishing, and/or quantifying at least one detectably labeled cell or component thereof in a sample comprising one or more cells or components thereof, at least one cell or component thereof of which is detectably labeled with at least two detectable labels, and, thus, has a level of sensitivity (i.e., a targeted cell or component thereof can be recognized in an overwhelming excess of very similar cells or components thereof) and a detection limit appropriate for non-amplified samples. The detection and enumeration is substantially more selective and sensitive than detection by using conventional flow cytometry techniques.

The present invention offers advantages over currently available detection means in that it enables the multiplexed detection and enumeration of cells or components thereof in the presence of antibody-conjugated detectable fluorescent labels, while avoiding the conventional problem of "false positive" detection, attributable to fluorescent antibody aggregation (i.e., aggregation of antibody-conjugated detectable fluorescent labels together). The selectivity and sensitivity of the present invention is due in large part to the capacity for multiplexed and simultaneous detection of at least two detectable labels that are co-localized on a detectably labeled cell or component thereof. In this manner, "false positives" in detection and enumeration of detectably labeled cells or components thereof of interest can be minimized or eliminated by ensuring that only those cells or components thereof, which are simultaneously labeled with at least two detectable labels are counted, and that neither cells or component thereof, which are not simultaneously labeled with at least two detectable labels, nor aggregates of antibody-conjugated detectable fluorescent labels (e.g., that form in the sample) are counted. The present invention also offers the advantage over currently available detection means of allowing for multiplexed detection and enumeration of multiple different types of cells or components thereof, each with a unique combination of detectable labels.

Moreover, the present invention provides a compact, efficient, and cost-effective system for use in the method. In the system, detectable emissions from at least two detectable labels on a detectably-labeled cell or component thereof are projected substantially directly or directly onto the array of photomultiplier tubes, e.g., without any intervening beam splitters and/or fiber optic cables.

The method comprises:

(i) introducing a sample comprising one or more cells or components thereof, at least one cell or component thereof of which is detectably labeled with at least two detectable labels, into one or more flow cells of a flow cytometer, (ii) irradiating the sample with one or more light sources that are absorbed by the at least two detectable labels, the absorption of which is to be detected, and (iii) detecting simultaneously the absorption of light by the at least two detectable labels on the detectably labeled cell or component thereof with an array of photomultiplier tubes, which are operably linked to two or more filters that selectively transmit detectable emissions from the at least two detectable labels, wherein the two or more filters and the array of photomultiplier tubes are operably linked to the one or more light sources by one or more optical bodies that project the detectable emissions from the at least two detectable labels to the two or more filters, wherein the simultaneous detection of absorption of light by the at least two detectable labels indicates the presence of a detectably labeled cell or component thereof in the sample.

The methods enable one or more detectably labeled cells or components thereof to be detected individually in a sample comprising one or more cells. For purposes of convenience, the term "cells" is intended to encompass cells, as well as viruses, viroids, and prions. In this regard, cells are defined herein to be any suitable cell, such as a eukaryotic cell or a prokaryotic cell, e.g., bacterial cell, baculoviral system, fungal cell (e.g., yeast), animal cell, such as an insect cell or a mammalian cell, or a plant cell. "Cellular components" is intended to encompass any and all of the foregoing even if not derived from a cell per se, such as any small molecules, carbohydrates, complex carbohydrates, nucleic acids (e.g., single-stranded, double-stranded, DNA, RNA, and hybrids thereof) and proteins (e.g., peptides, polypeptides and proteins), which can be glycosylated or glucosylated. In this regard, a sample comprising one or more cells or components thereof can comprise multiple small molecules, multiple molecules of nucleic acids, multiple molecules of proteins, or various combinations of the foregoing, wherein multiple includes two or more.

It will be appreciated that the present invention can be used to detect, distinguish or quantify such "cells or components thereof" as pathogens (or antigens associated with pathogens). A "pathogen" is an etiolytic agent that can cause disease. The present invention can be used to detect pathogens, such as viruses, viroids, bacteria, fungi, prions, parasites and the like. In this regard, the present invention can be used to detect pathogens, such as HIV, hepatitis A, B and C viruses, tuberculosis, chlamydia, gonorrhea, brachematis, a protein marker for Alzheimer's disease, *Neisseria gonorrhoeae*, *Vibrio cholerae*, syphilis (*Treponema pallidum*), Herpes viruses, human papilloma virus, tuberculosis (*Mycobacterium tuberculosis*), and group A *streptococcus*.

The present invention also can be used to detect, distinguish and/or quantify pathogens in any suitable sample, e.g., food, beverages (e.g., soda, bottled water, fruit juice, beer, wine and liquor products), water, pharmaceutical products, personal care products, dairy products and environmental samples. The present invention also can be used to detect pathogens in raw materials, equipment, products or processes used to manufacture or store food, beverages, water, pharmaceutical products, personal care products, dairy products or environmental samples. In this regard, the present invention can be used to detect and/or quantitate, e.g., (1) livestock diseases, such as *Taxoplasma gondii, Brucella abortus, Stephanuras dentatus, Mycoplasma bovis, Bovine rhinotracheitis, Maedi visna* virus, swine fever virus, *Leptospira interrogans*, and coronavirus; (2) toxins and pathogens, such as *Clostridium botulinum* neurotoxin A, B, E, F, or G, *Staphylococcus aureus*, enterotoxins A, B, C, D, E, aflatoxins B1, B2, B4 diol, M1, Q1, Ochratoxin, T-2 toxin, 3'-OH-T-2 toxin, T-2 tetranyltetraacetate, HT-2 toxin, group A trichothecenes, roridin A, diacetoxyscirpenol, deoxynlvalonel, 3-acetyl deoxynivalenol, deoxyverrucarol, zearalenone, sterigmatocystin, rubratoxin B, PR toxin, *Salmonella, Listeria monocytogenes, Escherichia coli, Vibrae* epp., *Yersinia enterocolitica*, and *Campylobacter jejuni*, (3) pesticides and compounds, such as dioxins, dibenzofurans, PCB's, triazine, aldrin, alachlor, atrazine, *Bacillus thuringensis* toxin, BAY SIR 8514, S-bioallethin, chlorosulfuron, cyanzine, 2,4-D, DDT, dichlorfop-methyl, dieldrin, difubenzuron, endosulfon, iprodione, kepone, maleate hydrazide, metalaxyl, oxfendazole, parathlon, panoxon, paraquat, pentachlorophenol, 2,4, 5-T, terbutryn, triadimefon, and warfarin; and (4) anabolic agents, such as 17β-estradiol, estrogen, testosterone, 17.alpha.-methyltestosterone, progesterone, trenbolone, diethylstilbestrol, hexoestrol, and zeronat.

The present invention also can be used to detect, distinguish and/or quantify pathogens in clinical samples, clinical specimens, clinical environments, and equipment, fixtures and/or products used to treat humans or animals. In this regard, the detection, identification and/or quantitation of certain organisms is particularly useful where these organisms comprise a group of pathogens for which a contamination limit applies by industry standard or by governmental regulation. One such group of organisms is the bacterial pathogens of the United States Pharmacopoeia (USP bacteria). USP bacteria include *E. coli*, the *Salmonella* genus, *Pseudomonas aeruginosa*, and *Staphylococcus aureus*. Food, beverage and pharmaceutical products are routinely examined for the presence, absence or number of these USP bacteria. The method can be used to detect, distinguish and/or quantify one or more organisms of interest in a sample wherein the organisms are members of the bacterial species of *E. coli, Staphylococcus aureus, Pseudomonas aeniginosa, Pseudomonas cepatia, Pseudomonas fluorescens*, or organisms of a bacterial genus including the *Salmonella* genus, *Bacillus* genus or *Pseudomonas* genus.

Suitable "cells or components thereof" for use in the present invention also include such cells as bioterrorism-related pathogens as, e.g., Anthrax spores (*Bacillus anthracis*), Ebola virus, *Staphylococcus aureus* enterotoxin B, Yellow fever virus, cloned protein toxins (e.g., snake toxins and scorpion toxins), Lassa fever virus, Ricin, and *Yersinia pestis*.

The present invention also can be used to detect, distinguish, and/or quantify such "cells or components thereof" as disease-associated cells or components thereof. In this regard, it will also be appreciated that the present invention can also be used for diagnostic purposes, through detection of cell antigens that are associated with disease and/or disorders. Accordingly, the term "cell" includes, for example, virally-infected cells (e.g., HIV-infected cells and hepatitis-infected cells) and cancer cells (e.g., cells derived from such cancers as leukemia, as well as lung, stomach, skin, brain, liver, prostate, testes, bone marrow, bone, breast, and intestinal cancer). In this regard, the detectable labels used in the context of the present invention can be specific for such cellular antigens as prostate-specific antigen (associated with prostate cancer), BRCA-1 and BRCA-2 antigens (associated with many adenocarcinomas, including breast cancer, lung cancer, and pancreatic cancer), CA125 (associated with ovarian cancer), aberrant myelin basic protein (associated with Alzheimer's disease), gp120 (associated with HIV infection and AIDS), MUC-1 (associated with breast cancer), EBNA-1 (associated with Epstein Barr Virus infection), CA19.9 (associated with colorectal, stomach, and pancreatic cancers), TAG-72 (associated with ovarian, stromal, and pancreatic cancers), and p53 (associated with various cancers).

The terms "detect," "distinguish" and "quantify" are used collectively herein to encompass any and all methods associated with identifying the presence and/or absence of one or more detectably labeled "cells or components thereof" in any suitable sample, as defined herein. In this regard, any desired diagnoses, treatments, purification processes, and/or production processes that are reasonably based upon the methods of detecting, distinguishing, and/or quantifying one or more detectably labeled "cells or components thereof," as defined herein, are contemplated.

By "detectably labeled" is meant that the cell or component thereof is labeled with a means of detection. Any suitable means of detection can be used. Such means are known in the art. Preferably, the means of detection is a fluorescent label. The labeling of a cell or component thereof with a means of detection is within the ordinary skill in the art. As an illustrative example, affinity-based fluorescent labels can be employed, such as fluorescent-labeled antibodies, fluorescent-labeled DNA, fluorescent-labeled RNA, cell-surface binding probes, or other types of fluorescent compounds. As is also known, such labels can be attached to the cell or component thereof by direct labeling or by indirect attachment, such as by sandwich labeling. In the context of the present invention, "detectably labeled" will also be used to encompass cells or components thereof that are naturally detectable, such that they do not need to be labeled with a detection means. For example, certain nucleic acids and proteins can fluoresce under certain conditions. Preferred fluorescent labels include those fluorescent dyes that absorb and fluoresce at red wavelengths, in order to minimize interference from any potential native fluorescence from cells or components thereof tested, due to the fact that few naturally occurring molecules absorb in the red and near-infrared spectral regions.

It is suitable to utilize 2 or more (e.g., 3 or more, 4 or more, 6 or more, 8 or more, or even 10 or more) different detectable labels in the context of the present invention. Moreover, it is suitable, for example, to use two or more different detectable labels, which target different cellular components (e.g., one fluorescent label that binds specifically to a cell-surface antigen and one fluorescent label that binds specifically to DNA). For example, Cy™ 5.5 (Amersham Biosciences, Piscataway, N.J.) and SYTO™ 61 (Invitrogen, Carlsbad, Calif.) can be used in the present invention. While Cy™ 5.5, which has a maximum fluorescence intensity at 694 nm, can be attached to antibodies for immunorecognition-based cellular (e.g., bacterial) identification, SYTO™ 61, which has a maximum fluorescence intensity at 675 nm, is a cell-permeable, DNA stain. Moreover, the fluorescent labels phycoerytherin and fluorescein isothiocyanate are suitable for use in the present invention.

FIG. 1 illustrates an example system for detections of cells or components thereof, in accordance with an embodiment of the present invention. In particular, the example system is shown to comprise a flow cell 10 into which a sample 12 comprising one or more cells or components thereof are introduced, a light source or laser 14 which projects through a band pass filter 16 upon the contents of the flow cell 10. The example system also comprises a sheath flow component 20 having a regulator 22, a sheath solution container 24, an air cylinder 26, and a flow sensor 28. Moreover, the example system comprises a core flow component 30 having a syringe pump 32, a sample carrier solution container 34, and a sample injection component 36. The example system also comprises an optical body 40 having an objective lens 42, an edge filter 44, and a notch filter 46, which transmit detectable emissions from at least two detectable labels on the one or more cells or components thereof in the sample 12 in the flow cell 10 to an array of photomultiplier tubes 100, having a first set 102 of at least eight PMT's and a second set 106 of at least eight PMT's (with each set of PMT's 102 and 106 having different types of filters thereon). The example system also comprises a custom circuit board 200, which has outputs to a computer 300 with a computer board.

The one or more flow cells 10 used in the context of the present invention can be any suitable flow cell (e.g., sheath-flow sample cell) for irradiation of a sample comprising one or more detectably labeled cells or components thereof. Moreover, it is contemplated in the present invention to have multiple parallel or non-parallel flow cells for the passing of identical, substantially identical, or different samples at identical (e.g., substantially identical) times for detection and/or enumeration of one or more detectably labeled cells or components thereof. In this regard, the present invention can comprise two or more flow cells, e.g., 3 or more, 4 or more, 6 or more, 8 or more, or even 10 or more flow cells. As know in the art, the flow cell used in the context of the present invention can be made out of any suitable material. Preferably, the flow cell is a 250 µm, square-bore quartz cell. Most preferably, the flow cell is a 250 µm, square-bore quartz cell, which employs hydrodynamic focusing through utilization of a pneumatically driven sheath of water (i.e., sheath flow).

Any suitable means can be used to introduce a sample into the one or more flow cells. For example, a syringe pump 32 can be used for sample introduction.

Any one or more light sources 14 (e.g., one or more lasers or laser diodes) can be used in the context of the present invention to irradiate the at least two detectable labels. Desirably, the one or more light sources 14 comprise or consist essentially of one or more (e.g., two or more, three or more, five or more, or even a full spectrum of) wavelengths of light that will be absorbed by the at least two detectable labels, the absorption of which is to be detected. Which wavelength(s) of light will be absorbed by the at least two detectable labels can be determined using a standard absorption spectrometer. Preferably, the light directed at the sample is red light, e.g., a red laser diode. It is suitable, for example, for the light source 14 to be a 635-nm, 12.5 mW diode laser module, such as one packaged with an integrated drive circuit, for fluorescence excitation.

The one or more light sources 14 used in the context of the present invention can be positioned in any suitable orientation around the flow cell 10, such that the sample passing through the one or more flow cells 10 can be suitably irradiated. It is suitable, for example, for the one or more light sources 14 to be circumferentially and perpendicularly arranged relative to the one or more flow cells 10 in the same plane. Alternatively, it is suitable for the one or more light sources 14 to be arranged in different planes, non-perpendicularly, and/or non-circumferentially. Moreover, it is suitable, for example, for the one or more light sources 14 to have a substantially identical (e.g., identical) focal region in the one or more flow cells 10, e.g., such that individual cells or components thereof in a sample 12 can be irradiated simultaneously by two or more, e.g., three or more, four or more, six or more, or even eight or more light sources 14.

By "detectable emissions" is meant any form of energy that is emitted from a detectable label following irradiation or excitation of the detectable label with one or more light sources 14, which can be detected. For example, "detectable emissions" is meant to encompass any single wavelength or multiple wavelengths of fluorescent light that is/are emitted upon irradiation of a fluorescent detectable label.

"Optical bodies" 40 are defined herein to be any suitable optics for collecting detectable emissions from at least two detectable labels and passing, projecting, and/or channeling the detectable emissions to an array of photomultiplier tubes. In this regard, the one or more optical bodies 40 used in the context of the present invention can be any suitable optical bodies. Preferably, the one or more optical bodies 40 comprise a microscope objective lens 42 (e.g., a 20× microscope objective). It is also preferable for the one or more optical bodies 40 used in the context of the present invention to comprise an edge filter 44 (e.g., a 643 nm edge filter) and/or a holographic notch filter 46 (e.g., a 635 nm holographic notch filter) to block scattered laser light. In one embodiment, the one or more optical bodies 40 comprise fiber optic cables (e.g., a 6 to 1 bundle of fiber optic cables), which collect and channel detectable emissions from at least two detectable labels. In another embodiment, the one or more optical bodies 40 project the detectable emissions from at least two detectable labels on a cell or cellular component of interest in a sample 12 directly (i.e., without use of mechanical means) or substantially directly or directly to two or more filters that selectively transmit the detectable emissions to an array of photomultiplier tubes (PMT's) 100. Preferably, the one or more optical bodies 40 do not comprise beam splitters and/or optic cables (e.g., fiber optic cables). This embodiment is preferred, for example, because it reduces the size and cost of the method and system and makes the system more effective and/or efficient.

The two or more filters used in the context of the present invention can be any suitable filters. In this regard, the process of choosing appropriate filters to correspond to the particular at least two detectable labels used in the present invention is well within the ordinary skill in the art. Preferably, the two or more filters used in the context of the present invention are filters optimized to detect fluorescent emission bands specific to the emission spectrum of the detectable emissions of the at least two detectable labels. Suitable bandpass filters include, for example, 650 nm, 20 nm bandwidth and 700 nm, 20 nm bandwidth bandpass filters. Preferably, the two or more filters are operably linked to both (i) the one or more optical bodies 40 and (ii) an array of PMT's 100, such that, e.g., one or more filters (i.e., "first filters") selectively transmit the detectable emissions (e.g., fluorescent wavelengths) from one or more irradiated detectable labels to one subset of PMT's in the array 102, while one more different filters (i.e., "second filters") selectively transmit the detectable emissions (e.g., fluorescent wavelengths) from one or more different irradiated detectable labels to a different subset of PMT's in the array 106. A "subset of PMT's" in an array, in this regard, can be a single PMT or, alternatively, can be a combination of two or more PMT's, e.g., three or more PMT's, four or more PMT's, five or more PMT's, six or more PMT's, or even seven or more PMT's (e.g., eight or more, ten or more, or even twelve or more PMT's). For example, a "first filter" can transmit detectable emissions from an irradiated detectable label to a combination of eight PMT's 102, and a "second filter" can simultaneously transmit detectable emissions from a second irradiated detectable label to a different combination of eight PMT's in the array 106. In this regard, the two or more filters function to select the color of light that falls on each half of the PMT array. For example, half of the PMTs of an array can be covered with a filter that transmits fluorescence from the antibody stain (Cy™ 5.5) and the other half of the PMT's of the array can be covered with a filter that transmits DNA stain (SYTO™ 61) fluorescence. This embodiment is illustrated in FIG. 1, wherein "Laser" 14 is a 635-nm, 12.5 mW diode laser module packaged with an integrated drive circuit, "Flow Cell" 10 is a sheath-flow sample cell consisting of a 250 µm, square-bore quartz cell, "Objective 20×" 42 is a 20× microscope objective, "Edge Filter" 44 is a 643 nm edge filter, "Notch Filter" 46 is a 635 nm holographic notch filter, "PMT Array" 100 is a detector comprised of a linear array of sixteen multi-alkali photocathodes that have a sensitivity range from 350 nm to 850 nm, "Cy™ 5.5 Filter" represents band-pass filters covering eight of the sixteen multi-alkali photocathodes of the PMT array 102, which are selective for lighted emitted from Cy™ 5.5 fluorescent detectable labels, "SYTO™ 61 Filter" represents band-pass filters covering eight of the sixteen multi-alkali photocathodes of the PMT array 106, which are selective for light emitted from SYTO™ 61 fluorescent detectable labels, "Filter 1 Signal" and "Filter 2 Signal" represent parallel circuits for processing signals from the Cy™ 5.5 Filter and the SYTO™ 61 Filter, "Custom Circuit Board" 200 represents the circuit board for processing PMT outputs, and "Output 1 TTL Pulse," "Output 2 TTL Pulse," and "AND Output," represent channels for transmittance of positive digital output pulses, respectively, from "Filter 1 Signal," "Filter 2 Signal," and from both concurrently.

The PMT's used in the context of the present invention can be any suitable PMT's. It is suitable, for example, for PMT's to be multi-alkali photocathodes that have a sensitivity range from about 350 nm to about 850 nm. The PMT's are collectively referred to herein as an "array" (e.g., a multi-anode array) of PMT's. In this regard, the "array" of PMT's can comprise any suitable number of PMT's. It is suitable, for example, for the array to comprise two or more PMT's, three or more PMT's, four or more PMT's, six or more PMT's, eight or more PMT's, ten or more PMT's, twelve or more PMT's. Most preferably, the array of PMT's comprise sixteen or more, e.g., 24 or more PMT's, 40 or more PMT's, 80 or more PMT's, or even 200 or more PMT's. In this regard, the number of PMT's that are operably linked with individual filters is important, in that the strength of the detection of emissions by particular irradiated detectable labels can be increased by choosing the appropriate number of associated PMT's for each operably linked filter (e.g., choosing to associate eight PMT's with each type of bandpass filter). In this manner, background noise can be reduced to a minimum. Choosing the number of PMT's to be operably linked to particular filters for use in the context of the present invention is well within the ordinary skill in the art.

Figure 3:
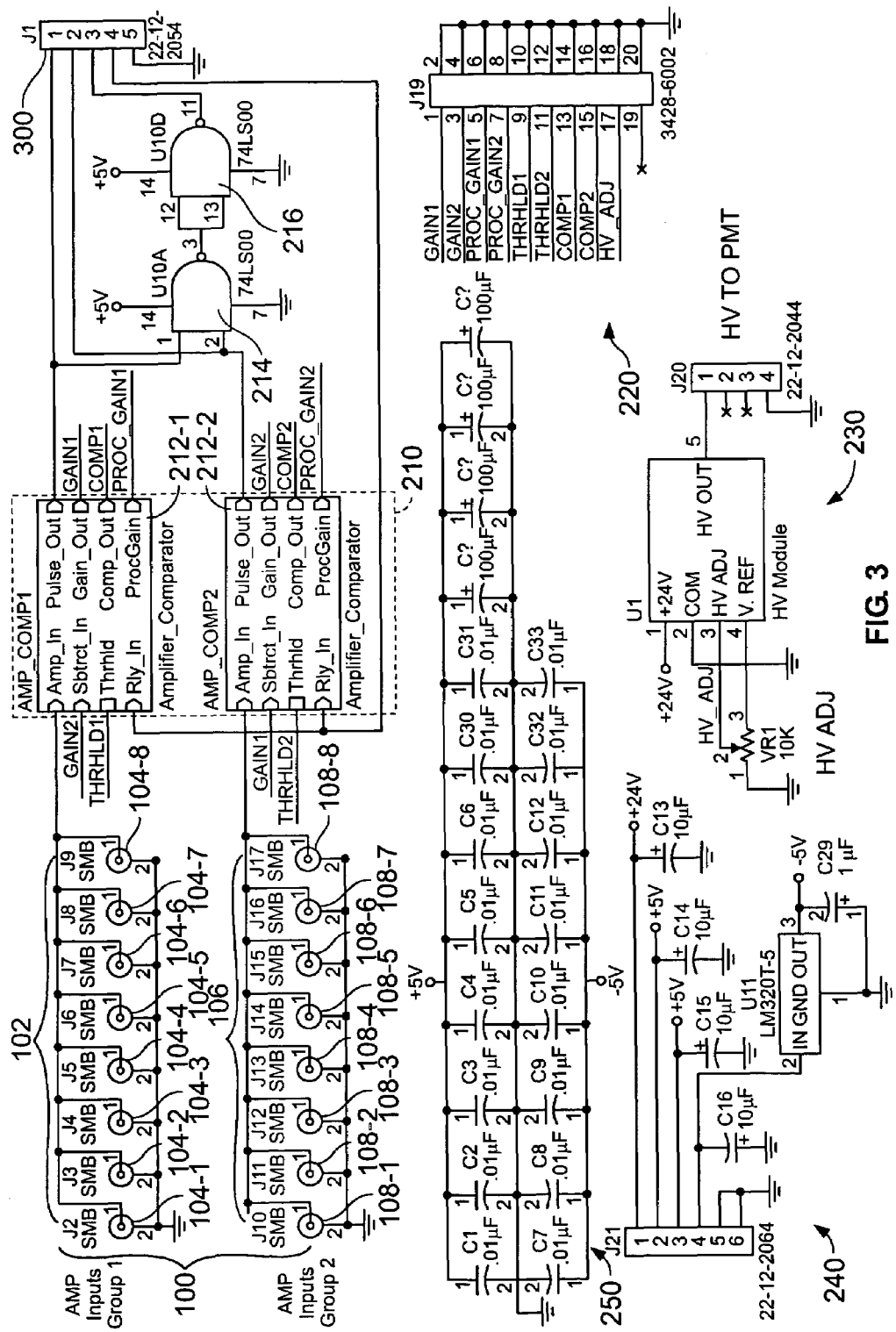
FIG. 3 is a diagram depicting an example layout of the "Custom Circuit Board" shown in FIG. 1 for performing the parallel processing and combining of signals from two sets of eight photomultiplier tubes by two identical circuits.

Processing of the signals from the array of PMT's (e.g., multi-anode array of multi-alkali photocathode PMT's) can be performed by any suitable circuit (or custom circuit) board. An example of a suitable circuit board layout is provided in FIG. 3. In particular, FIG. 3 illustrates PMT's 100 in the form of array 102, which comprises eight PMT's ("104-1" through "104-8"), and array 106, which comprises eight PMT's ("108-1" through "108-8"), which, in this example, are operably-connected to circuit board 200 comprising two amplifier-comparator circuits 212-1 and 212-2, an AND gate 214, and an Inverter 216, which is operably-connected to a computer device 300 (only partially depicted in FIG. 3). A more detailed illustration of suitable amplifier-comparators 210, for use as any or all of 212-1, 212-2 . . . 212-n is provided in FIGS. 4A and 4B. In particular, for example, the amplifier comparator 210 can include an "offset & filter" circuit 214, a "gain" circuit 215, a "mixer" circuit 216, a "threshold" circuit 217, and a "pulse stretcher" circuit 218.

In one embodiment, as illustrated in FIG. 3, the circuit board 200 can further include a signal monitor circuit 220, a high voltage module 230, a power circuit 240, and bypass capacitors 250. The power circuit 240 can provide the various +5V, −5V, and +24V DC outputs for the circuitry, as illustrated. A series of bypass capacitors 250 can be connected across the +5V and −5V terminals, as can be appreciated by one of skill in the art. As further indicated, the high voltage module 230 receives the +24V DC and adjusts that voltage as appropriate to provide the high voltage signal to the PMT's 100. The signal monitor circuit 220 provides signals to, and receives signals from, the amplifier-comparator circuits 210. In particular, the signal monitor 220 monitors signals "gain 1" and "gain 2" to the amplifier-comparator circuits 210, and receives the signals "process gain 1" and "process gain 2" from the amplifier-comparator circuits 210. The signal monitor 220 also outputs the "threshold" signals ("threshold 1" and "threshold 2") to the amplifier-comparator circuits 210, and receives the "comp 1" and "comp 2" signals from the amplifier-comparator circuit 210. Furthermore, the signal monitor 220 also outputs a high voltage adjustment signal to the high voltage module 230. The signal monitor 220 can adjust the threshold levels ("threshold 1" and "threshold 2") as necessary based on its monitoring of the signals "Gain 1," "Gain 2," "Process Gain 1," "Process Gain 2," "Comp 1," and "Comp 2," as are provided by the amplifier-comparator circuits 210. The signal monitor 220 can be any type of processor or controller, as would be understood by one of skill in the art. Furthermore, it is noted that, although the circuits, such as the signal monitor 220, high voltage module 230, power circuit 240, and bypass capacitors 250, are illustrated in this example as being on the circuit board 200, these components can be on separate circuit boards or part of other modules, as can be appreciated by one of skill in the art.

Figure 4A:
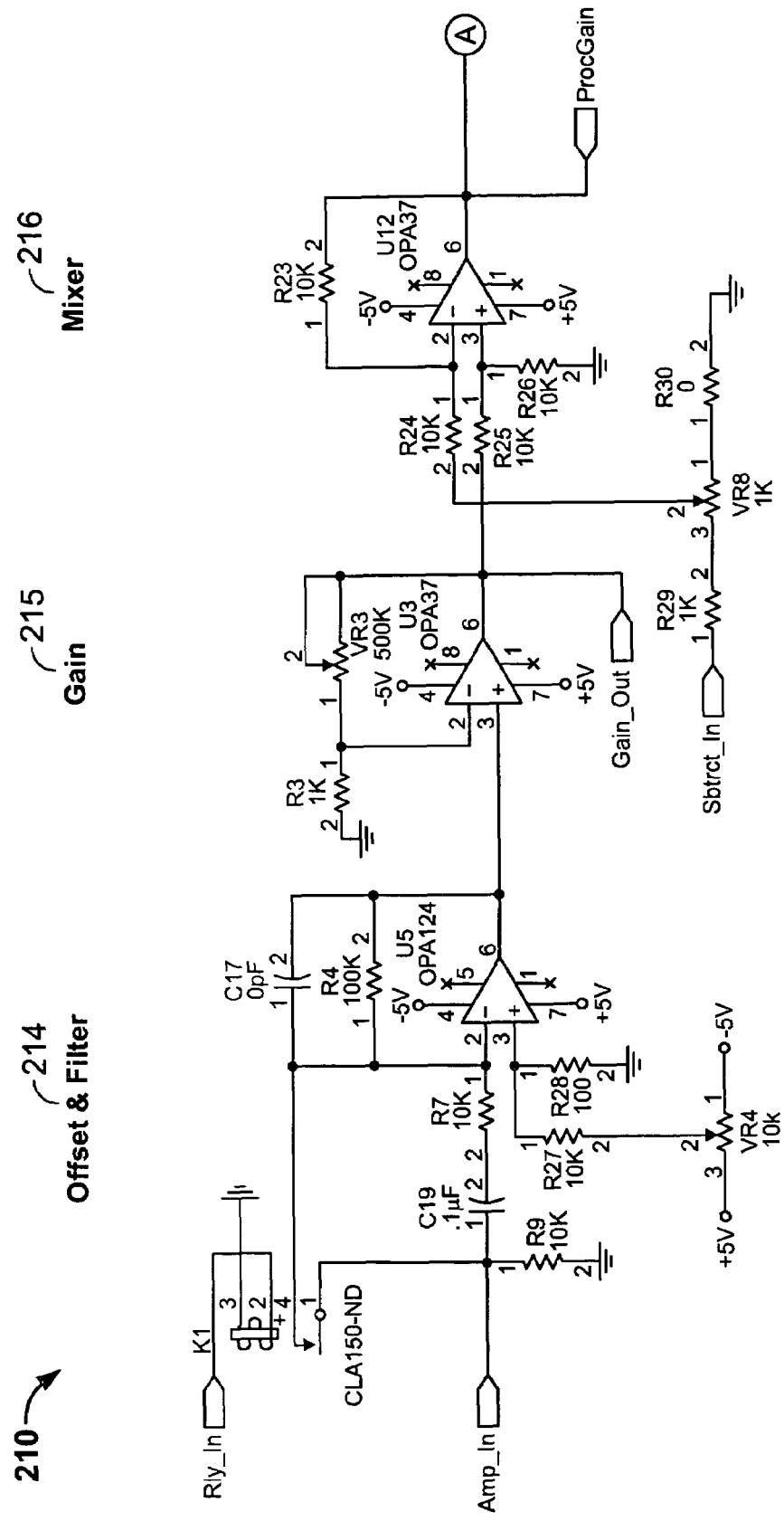
FIGS. 4A and 4B, in combination, represent a diagram depicting an example of an amplifier-comparator of the example "Custom Circuit Board" shown in FIG. 3.
Figure 4B:
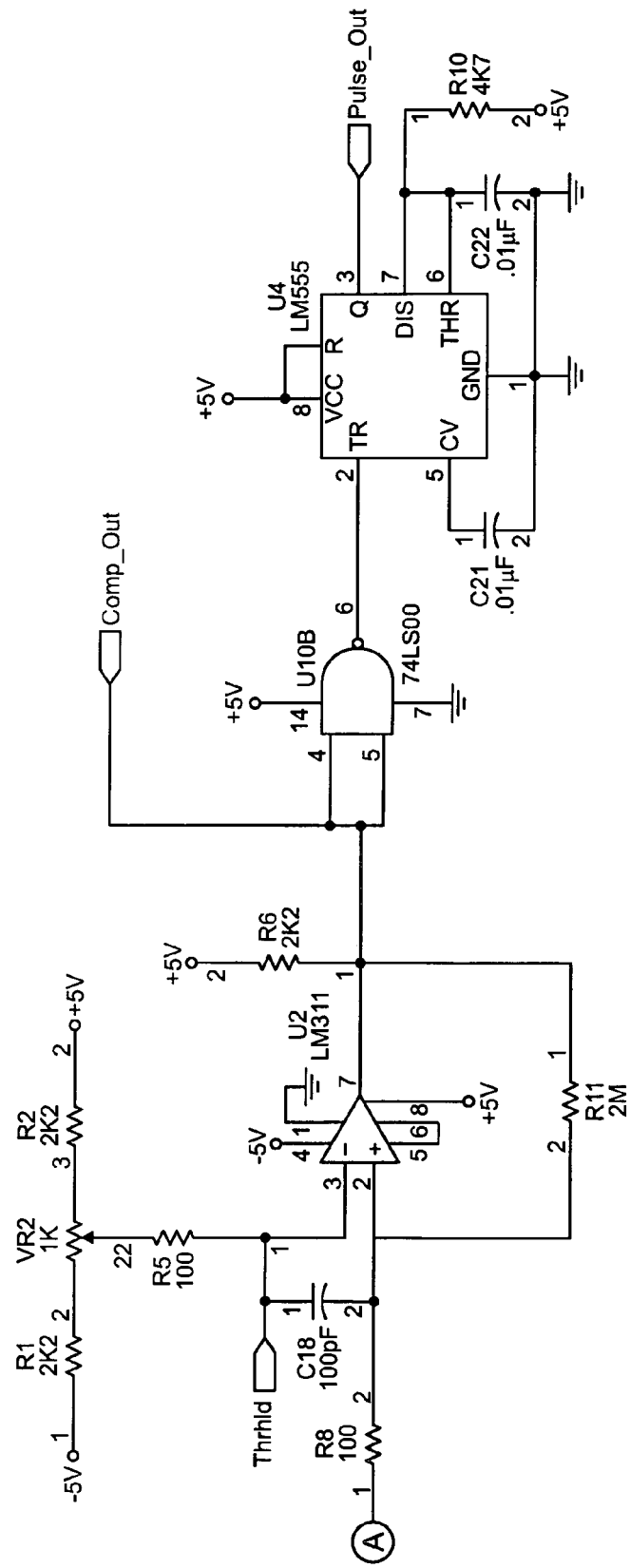

It is suitable, for example, for the signals from two or more subsets of PMT's in an array to be combined and processed in parallel by two or more identical or substantially identical circuits, e.g., for the signals from two subsets of eight PMT's to be combined and processed in parallel by two identical circuits, as is illustrated in FIGS. 4A and 4B.

Figure 5:
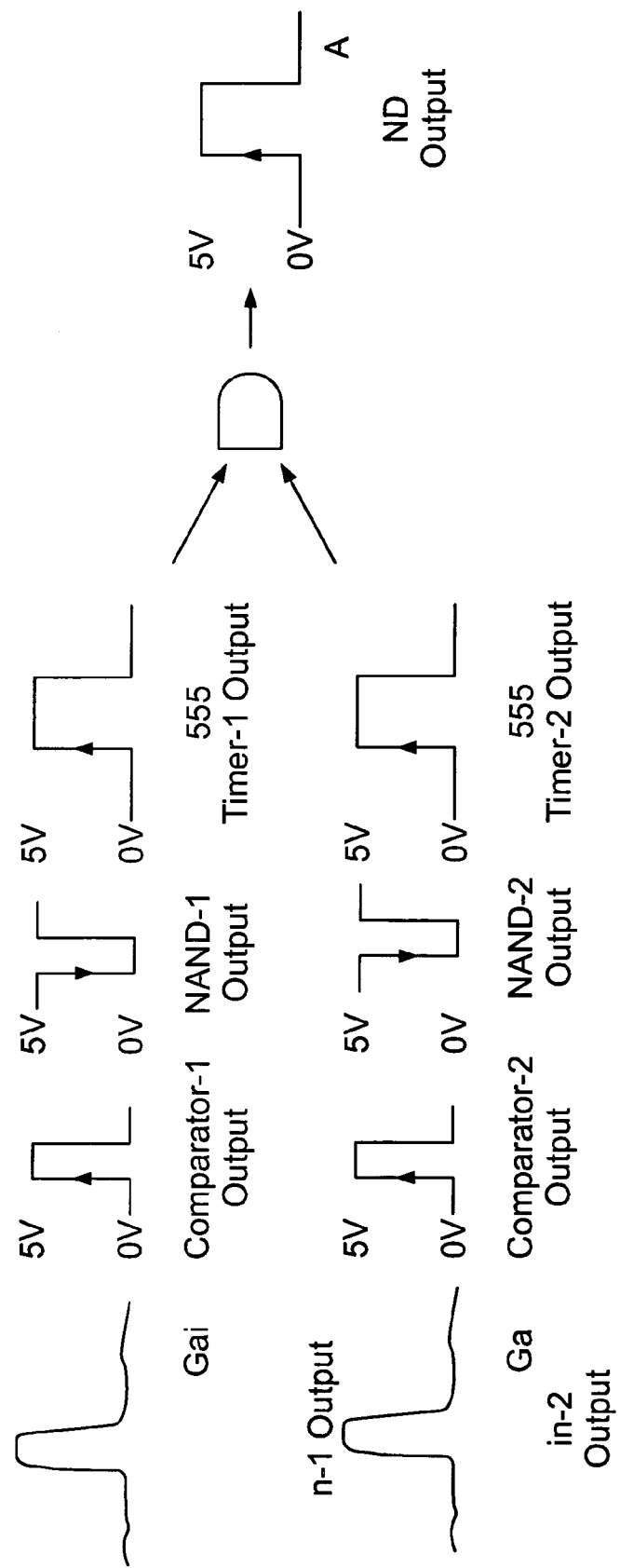
FIG. 5 is a diagram depicting digital output pulses from two channels of the "Custom Circuit Board" of FIG. 1.

Any suitable number of circuits can be utilized in the context of the present invention to amplify pulsed PMT outputs and to distinguish background noise from true detection events of the at least two detectable labels. In this regard, it is preferable that the circuits of the circuit board have the capacity to generate digital output pulses when and only when the magnitude of an incoming signal the first and/or second filter (e.g., first and/or second bandpass filter) exceeds a selectable threshold. The selection of appropriate thresholds for the two or more (e.g., three or more, four or more, six or more, or even eight or more) circuits is within the ordinary skill in the art, and is based on a balancing of both the desire to maximize detection of irradiated detectable labels and the desire to minimize background noise. The digital pulses from the two or more circuits or channels preferably are sent (i.e., relayed or transmitted) to an AND gate. An "AND gate" is defined herein as a circuit, which generates an output signal only when input pulses corresponding to those PMT's detecting each of the at least two detectable labels are presented concurrently or substantially concurrently, as illustrated in FIG. 5. In this manner, the efficiency and effectiveness associated with detection and enumeration of detectably labeled cells or components thereof is increased or enhanced, due to the fact that the AND gate will only "fire" output signals when there is simultaneous or substantially simultaneous detection of all of the at least two detectable labels. This, in turn, will only occur when a cell or component thereof that is detectably labeled with at least two detectable labels passes through the detection region of the one or more flow cells used in the context of the present invention.

Figure 6:
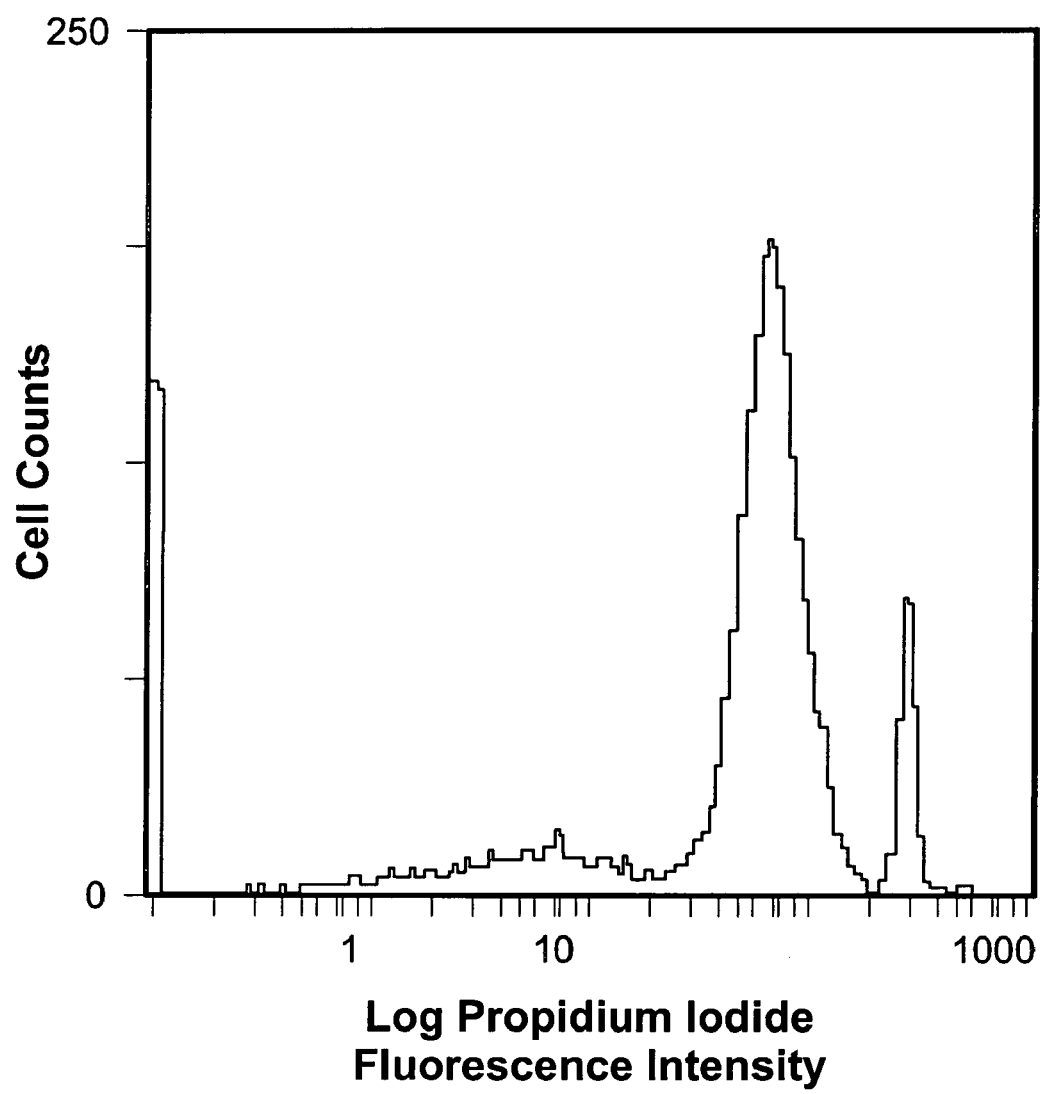
FIG. 6 is a graph of cell counts vs. log propidum iodide fluorescence intensity (counts).

The output pulses of the AND gate can be processed or computed in any manner known in the art. For example, the output pulses of the AND gate can be counted by a counter/timer board (National Instruments NI 6602) to determine the number of cells or components thereof (e.g., bacteria) in the sample, as illustrated in FIG. 6. The present method, thus, can be used for such purposes as testing products (e.g., food or beverages) for contamination, testing human fluid samples for diagnostic purposes.

In addition to the above method, the present invention provides systems for use in the above method. One embodiment of the system comprises:

(i) two or more flow cells, into which can be placed samples comprising one or more cells or components thereof, at least one cell or component thereof of which is detectably labeled with at least two detectable labels, (ii) one or more light sources that are absorbed by the at least two detectable labels, the absorption of which is to be detected, and (iii) an array of photomultiplier tubes, which are operably linked to two or more filters that selectively transmit detectable emissions from the at least two detectable labels, wherein the two or more filters and the array of photomultiplier tubes are operably linked to the one or more light sources by one or more optical bodies, which project the detectable emissions from the at least two detectable labels to the two or more filters.

Another embodiment of the system comprises:

(i) one or more flow cells, into which can be placed a sample comprising one or more cells or components thereof, at least one cell or component thereof of which is detectably labeled with at least two detectable labels, (ii) one or more light sources that are absorbed by the at least two detectable labels, the absorption of which is to be detected, and (iii) an array of photomultiplier tubes, which are operably linked to two or more filters that selectively transmit detectable emissions from the at least two detectable labels, wherein the two or more filters and the array of photomultiplier tubes are operably linked to the one or more light sources by one or more optical bodies, which project the detectable emissions from the at least two detectable labels to the two or more filters, wherein the optical bodies do not comprise optic cables.

Any suitable sample 12 containing any suitable one or more detectably labeled "cells or components thereof" can be used in the present inventive system, as discussed above with respect to the method. In this regard, the system can be used to detect, distinguish and/or quantify multiple different, substantially identical, or identical samples at substantially identical or identical times, wherein each sample 12 contains one or more different, substantially identical, or identical cells or components thereof.

The one or more flows cells 10 (e.g., two or more flow cells) used in the present system can be any suitable flow cell (e.g., sheath-flow sample cell) for irradiation of the one or more samples 12 comprising one or more detectably labeled cells or components thereof, as discussed above with respect to the method. In this regard, it is contemplated in the present system to have multiple substantially parallel or parallel or non-parallel flow cells for the passing of the multiple different, substantially identical, or identical samples containing one or more different, substantially identical, or identical thereof. Moreover, the present invention may comprise three or more flow cells, e.g., 6 or more, 12 or more, or even 16 or more flow cells. As noted above, the flow cell 10 used in the context of the present invention can be made out of any suitable material and any suitable means can be used to introduce a sample into the one or more (e.g., two or more) flow cells of the present system.

The one or more light sources 14 used in the present system can be any suitable light sources, as described above with respect to the present inventive method. Moreover, the one or more light sources 14 can be positioned in any suitable orientation around the one or more (e.g., two or more) flow cells 10, as described.

The one or more optical bodies 40 used in the present system can be any suitable optics for collecting detectable emissions from at least two detectable labels and passing, projecting, and/or channeling the detectable emissions to an array of PMT's 100, as discussed above. Preferably, the system has a suitable number of optical bodies to operably link the flow cells 10 of the system to the array of PMT's 100, such that the detection emissions from the at least two detectable labels is adequately directed to the array 100. In this regard, it is well within the ordinary skill of the art to determine how many optical bodies must be included in the system, e.g., one optical body for each flow cell, one optical body for each two flow cells, or even one optical body for each sixteen flow cells.

The two or more filters can be any suitable filters, as described above. Moreover, the two or more filters can selectively transmit the detectable emissions from at least two detectable labels to any suitable number of "subsets" of PMT's, which can be made out of any suitable material, and which are operably linked to any suitable filters, as described above with respect to the method. The system may further comprise any suitable number of circuits, preferably with an AND gate, as described above, and the output pulses of the AND gate can be processed or computed in any manner known in the art.

EXAMPLES

The present invention is further demonstrated by way of the following examples, which serve to illustrate the present invention but are not intended to limit its scope in any way.

SYTO™ 61 is a detectable fluorescent label, which is a cell-permeable, DNA stain, and which has an absorption maximum at 628 nm and a fluorescence maximum at 645 nm. Cy™ 5.5 is a detectable fluorescent label, which can be attached or conjugated to antibodies for immunorecognition-based bacterial identification, and which has a maximum fluorescence intensity at 694 nm and an absorption maximum at 675 nm. All bacteria used in the tests illustrated in Examples 1 and 2 were heat-killed.

Staining with Cy™ 5.5-labeled anti-$E.$ $coli$ O157:H7 antibody. $E.$ $coli$ was stained with Cy™ 5.5 detectable labels in the following manner: 50 µL of stock $E.$ $coli$ O157:H7 (~1×$10^9$ cells/mL) were diluted with 900 µL of phosphate-buffered saline (PBS) containing 0.05% Tween20 (Sigma, St. Louis, Mo.). 50 µL Cy™ 5.5-labeled anti $E.$ $coli$ O157:H7 antibody were added, and the solution was incubated at 37° C. for 1 hour with mild rotation (~85 rpm). Further dilution was done with PBS containing 0.05% Tween20.

Staining with SYTO™ 61 nucleic acid stain. 50 µL of stock $E.$ $coli$ O157:H7 (~1×$10^9$ cells/mL) were diluted with 920 µL of PBS containing 0.05% Tween20 (Sigma). Stock SYTO™ 61 dye solution was diluted 50× with deionized water. Thirty µL of diluted dye were added to $E.$ $coli$ O157:H7, and the solution was incubated at room temperature for 30 minutes. Further dilution was done with PBS containing 0.05% Tween20.

Dual staining with Cy™ 5.5 anti-$E. coli$ O157 antibody and SYTO™ 61 nucleic acid stain. 50 μL of stock $E. coli$ O157:H7 (~1×10$^9$ cells/mL) were diluted with 870 μL of PBS containing 0.05% Tween20. Fifty μL of Cy™ 5.5-labeled anti $E. coli$ O157:H7 antibody were added, and the solution was incubated at 37° C. for 1 hour with mild rotation (~85 rpm). Stock SYTO™ 61 dye solution was diluted 50× with deionized water and ~30 μL diluted dye were added to the incubated solution. Then, the solution was incubated at room temperature for 30 minutes. Further dilution was done with PBS containing 0.05% Tween20.

The following assay parameters were utilized in Examples 1 and 2: Sample loop: 500 μL; Sheath flow rate: 5-6 mL/min @ 3 psig air pressure; Syringe dispensation or core flow rate: 0.498 mL/min; Syringe push volume for each test: 2 mL; Time required for each test: ~4 min Sheath/Core flow ratio ~10-12; Calculated core diameter: (Core flow rate/Sheath flow rate)$^{1/2}$×(Flow channel diameter)=>~70 μm; Voltage applied to PMT: ~-900 V; Threshold voltage for SYTO™ 61 channel: 0.375 V and Cy™ 5.5 channel: 0.365 V.

Example 1

This example demonstrates the efficiency and effectiveness of the present invention in quantifying cells (e.g., bacteria), due to a lessening of "false positive" detections.

$E. coli$ O157:H7 and $Staphylococcus$ $epidermidis$ were stained with (i) SYTO™ 61, (ii) Cy™ 5.5-labeled anti-$E. coli$ O157:H7, or (iii) simultaneously with both detectable labels, and the number of counts in each of the three detection channels (i.e., the "SYTO™ 61 detection channel," the "Cy™ 5.5 detection channel," and the "AND gate channel") were measured. It was expected that the $Staphylococcus$ $epidermidis$ sample would only produce counts (i.e., "detection events") in the SYTO channel, due to the knowledge in the art that $Staphylococcus$ $epidermidis$ can not be stained by the Cy™ 5.5-labeled antibody, but can be stained by SYTO™ 61. Moreover, it was expected that $E. coli$ O157:H7 would produce counts or detection events in all three signal channels (i.e., the "SYTO™ 61 detection channel," the "Cy™ 5.5 detection channel," and the "AND gate channel"), due to the knowledge in the art that $E. coli$ O157:H7 can be stained by both detectable labels. Control samples were also run that did not contain any bacteria but were otherwise treated in the same manner as the other samples. The results are given in Table 1.

TABLE 1

| Sample | SYTO ™61 channel counts | Cy ™5.5 channel counts | AND gate counts | Expected AND gate counts for 500 μL sample loop |
|---|---|---|---|---|
| Control stained with SYTO ™61 | 403 | 88 | 79 | 0 |
| Control stained with antibody-conjugated Cy ™5.5 | 45 | 891 | 31 | 0 |
| Control-Dual Stained | 427 | 924 | 89 | 0 |
| $E.coli$ O157:H7 stained with SYTO ™61 | 25,171 | 621 | 232 | 0 |
| $E.coli$ O157:H7 stained with antibody-conjugated Cy ™5.5 | 158 | 26,021 | 103 | 0 |
| $E. coli$ O157:H7-Dual Stained | 26,732 | 27,679 | 26,028 | 500,000 |
| $Staphylococcus$ $epidermidis$ stained with SYTO ™61 | 15,356 | 463 | 187 | 0 |
| $Staphylococcus$ $epidermidis$ stained with antibody-conjugated Cy ™5.5 | 59 | 832 | 46 | 0 |
| $Staphylococcus$ $epidermidis$-Dual Stained | 14,197 | 776 | 102 | 0 |

Table 1 illustrates that dual staining (i.e., with Cy™ 5.5 and SYTO™ 61) and simultaneous detection via the "AND gate" reduce the number of false counts. In particular, as demonstrated in Table 1, while the Cy™ 5.5 control, dual-stained control, and the $Staphylococcus$ $epidermidis$ with Cy™ 5.5 samples do not bind with the Cy™ 5.5 detectable label, these samples exhibited relatively high Cy™ 5.5 channel counts (i.e., 89, 924, and 832, respectively), due in all likelihood to the detection of antibody aggregates. In contrast, the same Cy™ 5.5 control, dual-stained control, and the $Staphylococcus$ $epidermidis$ with Cy™ 5.5 samples exhibited relatively low "AND gate" counts (i.e., 31, 89, and 46, respectively), thus eliminating the detection of antibody aggregates.

Moreover, as demonstrated in Table 1, there is minimal cross-reactivity of anti-$E. coli$ O157 antibody with non-target bacteria. In particular, the $Staphylococcus$ $epidermidis$ was single- and dual-stained to detect any cross-reactivity of anti-$E. coli$ O157 antibody. Counts in the case of Cy™ 5.5 stained $Staphylococcus$ $epidermidis$ in the Cy™ 5.5 channel are similar to the Cy™ 5.5 staining control, which were due to Cy™ 5.5 anti-$E. coli$ O157 antibody aggregates. Thus, no significant AND gate counts were observed in the case of stained $Staphylococcus$ $epidermidis$, which indicates minimal cross-reactivity of anti-$E. coli$ O157 antibody with non-target bacteria.

In the case of SYTO™ 61-containing controls and SYTO™ 61-stained bacteria, higher AND gate counts were observed than were seen with the Cy™ 5.5 control and Cy™ 5.5-stained $Staphylococcus$ $epidermidis$. We attribute this to the overlapping of SYTO™ 61 fluorescence with the Cy™ 5.5 detection wavelength band. In contrast, Cy™ 5.5 fluorescence overlaps very little with the SYTO™ 61 detection band.

This example, thus, demonstrates that simultaneous detection of at least two detectable labels on a cell or component thereof, which is detectably labeled with at least two detectable labels, enhances the efficiency and effectiveness of cell detection and quantification, due to a lessening of "false positive" detections.

Example 2

This example demonstrates the efficiency and effectiveness with which the present invention can be used to selectively detect and count target cells (e.g., bacteria) in a sample containing a variety of cells.

Target bacterial cells (i.e., $E. coli$ O157:H7 dual-stained with both SYTO™ 61 and Cy™ 5.5-labeled anti-$E coli$ O157:

H7 antibody, as described above) and non-target bacterial cells (i.e., *Staphylococcus epidermidis* dual-stained with both SYTO™ 61 and Cy™ 5.5-labeled anti-*E coli* O157:H7 antibody, as described above) were mixed in the following ratios: (1) in a first sample, 50 μL of *E. coli* O157:H7 were mixed with 25 μL of *Staphylococcus epidermidis*, and (2) in a second sample, 50 μL of *E. coli* O157:H7 were mixed with 50 μL of *Staphylococcus epidermidis*. Next, the number of counts in each of the three detection channels (i.e., the "SYTO™ 61 detection channel," the "Cy™ 5.5 detection channel," and the "AND gate channel") were measured for the two samples. In this manner, the effect of an increasing concentration of non-target bacterial cells on the detection and quantification of dually-labeled target bacterial cells was determined.

The results of measurements of mixtures of *E. coli* O157: H7 and *Staphylococcus epidermidis* are given in Table 2.

TABLE 2

| Sample | Expected counts | SYTO™61 channel counts | Cy™5.5 channel counts | AND gate counts | SYTO™61 channel minus AND gate counts |
|---|---|---|---|---|---|
| 50 μL *E. coli* O157:H7 + 25 μL *Staphylococcus epidermidis* | *E. coli*: 500,000 Staph: 150,000 | 31,124 | 23,849 | 21,255 | 9,869 |
| 50 μL *E. coli* O157:H7 + 50 μL *Staphylococcus epidermidis* | *E. coli*: 500,000 Staph: 300,000 | 40,927 | 28,321 | 23,611 | 17,316 |

The number of counts in the SYTO™ 61 channel represent the total number of bacteria (target and non-target), whereas the Cy™ 5.5 channel counts represent the number of target bacteria and aggregated antibodies. As illustrated in Table 2, the number of counts in the SYTO™ 61 channel increased as the total number of bacteria (target and non target bacteria) increased, whereas the number of counts in the Cy™ 5.5 channel (target bacteria and aggregated antibody) remained roughly constant. The number of target bacteria alone is represented by the AND gate counts (i.e., which fires only when there are simultaneous signals presented in both SYTO™ 61 and Cy™ 5.5 channels). As illustrated in Table 2, the AND gate counts are lower than the Cy™ 5.5 channel counts. This is due an elimination of false count detection of antibody aggregates through utilization of simultaneous detection and the AND gate.

The number of non-target bacteria number was obtained by subtraction of AND gate counts (i.e., target bacteria) from SYTO™ 61 channel counts (i.e., target and non target bacteria). This number approximately doubled when the number of *Staphylococcus epidermidis* was doubled, while the AND gate counts showed only a small increase.

This example demonstrates the efficiency and effectiveness of the present invention in selectively quantifying target bacteria in the presence of non-target bacteria and antibody aggregates.

All sources (e.g., inventor's certificates, patent applications, patents, printed publications, repository accessions or records, utility models, and the like) referred to or cited anywhere in this document or in any drawing, Sequence Listing, or Statement filed concurrently herewith are hereby incorporated into and made part of this specification by such reference thereto.

The foregoing is an integrated description of the invention as a whole, not merely of any particular element or facet thereof. The description describes several preferred embodiments" of this invention, including the best mode known to the inventors for carrying it out. Of course, upon reading the foregoing description, variations of those preferred embodiments will become obvious to those of ordinary skill in the art. The inventors expect ordinarily skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law.

What is claimed is:

1. A method for detecting a detectably labeled cell or component thereof in a sample, which method comprises:
   (i) introducing a sample comprising one or more cells or components thereof, at least one cell or component thereof of which is detectably labeled with at least two detectable labels, into one or more flow cells of a flow cytometer,
   (ii) irradiating the sample with one or more light sources that are absorbed by the at least two detectable labels, the absorption of which is to be detected, and
   (iii) detecting simultaneously the absorption of light by the at least two detectable labels on the detectably labeled cell or component thereof with an array of photomultiplier tubes, which are operably linked to two or more filters that selectively transmit detectable emissions from the at least two detectable labels, wherein the two or more filters and the array of photomultiplier tubes are operably linked to the one or more light sources by one or more optical bodies, which do not comprise beam splitters or optic cables and which project the detectable emissions from the at least two detectable labels to the two or more filters,
   wherein the simultaneous detection of absorption of light by the at least two detectable labels indicates the presence of a detectably labeled cell or component thereof in the sample.

2. The method of claim 1, wherein the at least one cell or component thereof of the sample is detectably labeled with at least two detectable labels that bind to at least two different types of cell components.

3. The method of claim 2, wherein the at least two detectable labels comprise at least one detectable label that binds to a cell-surface antigen and at least one detectable label that binds to a nucleic acid.

4. The method of claim 1, wherein the array of photomultiplier tubes comprises a first set of at least eight photomultiplier tubes, which are operably linked to one or more first filters that selectively transmit detectable emissions from one of the at least two detectable labels to the first set of at least eight photomultiplier tubes, and a second set of at least eight photomultiplier tubes, which are operably linked to one or more second filters that selectively transmit detectable emissions from one of the at least two detectable labels to the second set of at least eight different photomultiplier tubes, wherein the detectable label detected by the first set of at least eight photomultiplier tubes is different from the detectable label detected by the second set of at least eight photomultiplier tubes.

* * * * *